US010219686B2

(12) United States Patent
Lin et al.

(10) Patent No.: US 10,219,686 B2
(45) Date of Patent: Mar. 5, 2019

(54) MEDICAL BITE BLOCK

(71) Applicant: National Yang-Ming University, Taipei (TW)

(72) Inventors: Chun-Li Lin, Taipei (TW); Yu-Tzu Wang, Taipei (TW); Chien-Kun Ting, New Taipei (TW); Wei-Nung Teng, Taipei (TW)

(73) Assignee: National Yang-Ming University, Taipei (TW)

( * ) Notice: Subject to any disclaimer, the term of this patent is extended or adjusted under 35 U.S.C. 154(b) by 160 days.

(21) Appl. No.: 15/181,794

(22) Filed: Jun. 14, 2016

(65) Prior Publication Data

US 2017/0238796 A1 Aug. 24, 2017

(30) Foreign Application Priority Data

Feb. 22, 2016 (TW) .............................. 105105181 A

(51) Int. Cl.
*A61B 90/16* (2016.01)
*A61M 16/04* (2006.01)
*A61B 1/24* (2006.01)
*A61B 1/00* (2006.01)
*A61B 1/273* (2006.01)
*A61M 16/06* (2006.01)
*A61M 16/08* (2006.01)

(52) U.S. Cl.
CPC ............ *A61B 1/24* (2013.01); *A61B 1/00154* (2013.01); *A61B 1/273* (2013.01); *A61B 90/16* (2016.02); *A61M 16/0493* (2014.02); *A61M 16/0495* (2014.02); *A61M 16/0666* (2013.01); *A61M 16/0816* (2013.01)

(58) Field of Classification Search
CPC ..... A61M 16/0493; A61B 90/16; A61B 17/24
USPC ......................................................... 600/238
See application file for complete search history.

(56) References Cited

U.S. PATENT DOCUMENTS

| 4,495,945 A * | 1/1985 | Liegner ............. A61M 16/0493 |
| | | 128/200.26 |
| 5,590,643 A * | 1/1997 | Flam ................. A61M 16/0488 |
| | | 128/200.26 |
| 6,851,424 B2 * | 2/2005 | Scopton ............. A61B 1/00154 |
| | | 128/200.26 |

(Continued)

*Primary Examiner* — Olivia C Chang
(74) *Attorney, Agent, or Firm* — Muncy, Geissler, Olds & Lowe, P.C.

(57) ABSTRACT

An integrated medical bite block is engaged by a user's teeth and installed into the user's mouth. The bite block includes a through passageway, an upper grove, and a lower grove. The through passageway is penetrating through the bite block. One end of the through passageway comprises an inlet opening, the other end comprises an oral opening. The oral opening is connected with the user's mouth. An upper surface of the bite block provides the upper grove configured for receiving one or more upper teeth (maxillary teeth) of the user, and a lower surface of the bite block provides a lower grove configured for receiving one or more lower teeth (mandibular teeth) of the user. One distance between the lower grove and the oral opening is greater than the other distance between the upper grove and the oral opening, thereby the invention serves to extend forward the mandible and reposition a malposition between the mandible and the maxilla of the user.

6 Claims, 6 Drawing Sheets

(56) References Cited

U.S. PATENT DOCUMENTS

| | | | | |
|---|---|---|---|---|
| 2007/0006878 A1* | 1/2007 | Mackey | ............ | A61M 16/0488 |
| | | | | 128/200.26 |
| 2010/0132700 A1* | 6/2010 | Filipi | ................. | A61B 1/00154 |
| | | | | 128/200.26 |
| 2010/0317987 A1* | 12/2010 | Inoue | ................ | A61M 16/0488 |
| | | | | 600/543 |

* cited by examiner

MEDICAL BITE BLOCK

CROSS-REFERENCE TO RELATED APPLICATIONS

This Non-provisional application claims priority under 35 U.S.C. § 119(a) on Patent Application No(s). 105105181 filed in Taiwan, Republic of China Feb. 22, 2016, the entire contents of which are hereby incorporated by reference.

FIELD OF THE INVENTION

The present invention relates to a medical bite block, especially relates to a medical bite block for installing into the user's mouth during endoscopic inspection, endoscopic inspection using total intravenous anesthesia (i.e., painless endoscopy) or gastroscopy, then the user's lower jaw extends forward beyond the upper jaw and forms a malposition between his lower jaw and upper jaw during inspection. Hence, the doctor can facilitate to insert the endoscope smoothly into the user's mouth and open the patient's airway at the same time.

BACKGROUND OF THE INVENTION

The traditional and existed bite block generally serve to hold the patient's mouth open and provide an access path for the endoscope inserted into the patient's month to obtaining a visual inspection. At the same time, the patient need to be lying on their right side or left side, i.e. right lateral recumbent position or left lateral recumbent position. However, when the patient is in deep state of unconsciousness during endoscopic inspection using intravenous anesthesia (i.e., painless endoscopy), the upper airway often obstructs due to tongue falling back after induction of anesthesia.

Moreover, some anesthetic drugs would cause a dose-dependent reduction in ventilatory minute volume. On the other hand, some anesthetic drugs would result in airway obstruction and prevent the passage of air. As mentioned above, the patient receiving these anesthetic drugs would have high risk of respiratory related complications such as hypoventilation, hypoxemia and apnea. The patient usually lied down laterally to avoid a blockage in the airway in clinical practice, thus the risks of sedated endoscopic inspection would be decreased. In order to avoid hypoxia due to upper airway obstruction occurring by the tongue falling back after induction of anesthesia in patients, the doctor managed and monitored anesthesia care via the patient's physiologic parameters, such as peripheral oxygen saturation, heart rate, blood pressure, etc., Unfortunately, few patients still suffered from hypoxia, stroke even death during endoscopic inspection.

Existed bite blocks only serve to hold the patient's mouth open and protect the endoscopic device from injury. However, existed bite blocks did not prevent airway obstruction occurring by the tongue falling back. On the other hand, there is a longer distance to nasal cavity and upper respiratory tract from an opening of channel. As a consequence, the patient did not get enough oxygen through the opening of channel. This means that the existed medical bite blocks for endoscopy in clinical practice could not reduce the above mentioned risks and could not solve the above mentioned problems during endoscopic examinations.

Accordingly, how to develop a bite block which could prevent hypoxia due to respiratory inhibition and airway obstruction by the tongue falling back during anesthesia is needed for medical professionals performing endoscopic examinations.

SUMMARY OF THE INVENTION

In the view of the foregoing disadvantages inherent in the known types of bite block now present in the prior art, it is an important subject to provide a bite block which is easily bitten steadily without using straps, without falling and can maintain a malposition of mouth shape between upper jaw (maxilla) and lower jaw (mandible) for a patient performed upon medical inspection, clinical practice and anesthesia.

Accordingly, one objective of the present invention is to solve current problem of existing medical bite blocks during medical inspection, clinical practice and anesthesia. The present invention provides a medical bite block for user's lower jaw protruding forward and his upper jaw still stayed at a resting position in order to form a malposition of mouth, so that he could avoid the tongue fall down caused upper airway obstruction, so that the risks of endoscopic examinations during anesthesia could be decreased. Thus, the problem of the conventional technique is thereby solved.

The following presents a simplified summary of the disclosure in order to provide a basic understanding to the reader. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

It is an objective of the present invention to solve the above-described problems in the conventional techniques and thus to provide a medical bite block, which is integrated as one-piece and is provided for a user to bite and is inserted into the user's mouth, wherein the medical bite block includes: a through passageway, which is penetrating through the medical bite block, wherein one end of the through passageway comprises an inlet opening, the other end comprises an oral opening, wherein the oral opening is used to connected with an oral cavity of the user. An upper biting groove, wherein an upper surface of the medical bite block provides the upper biting groove, and a lower biting groove, wherein a lower surface of the bite block provides the lower biting groove. Wherein a second distance between the lower biting groove and the oral opening is greater than a first distance between the upper biting groove and the oral opening, thereby the lower biting groove is away from the oral cavity of the user relative to the upper biting groove and provides a first malposition between the lower biting groove and the upper biting groove.

Furthermore, in accordance with another preferred embodiment of the present invention, the upper biting groove is perpendicular to an axis of the through passageway, which further comprises a first longitudinal surface, the lower biting groove is perpendicular to the axis of the through passageway, which further comprises a second longitudinal surface, wherein the first longitudinal surface and the second longitudinal surface is not overlapped but is corresponded, and the second distance between the second longitudinal surface and the oral opening is greater than the first distance between the first longitudinal surface and the oral opening.

Furthermore, in accordance with another preferred embodiment of the present invention, wherein a third distance between the first longitudinal surface and the second longitudinal surface is 1 to 12 mm along with the axis of the through passageway.

Furthermore, in accordance with another preferred embodiment of the present invention, which further comprises an oral inspiration and expiration part, wherein the oral inspiration and expiration part is located inside the inner wall of the through passageway as a ring shape.

Furthermore, in accordance with another preferred embodiment of the present invention, wherein the oral inspiration and expiration part further comprises a proximal inspiration channel and a distal expiration channel, wherein the proximal inspiration channel and the distal expiration channel form a second malposition with each other, wherein the proximal inspiration channel and the distal expiration channel are located adjacent to each other formed as a ring shape situated at the oral inspiration and expiration part.

Furthermore, in accordance with another preferred embodiment of the present invention, wherein a fourth distance between the proximal inspiration channel and the oral opening is shorter than a fifth distance between the distal expiration channel and the oral opening, and the distal expiration channel is away from the oral cavity of the user relative to the proximal inspiration channel and form the second malposition with each other.

Furthermore, in accordance with another preferred embodiment of the present invention, which further comprises a central partition member, wherein the central partition member is used to separate the proximal inspiration channel from the distal expiration channel.

Furthermore, in accordance with another preferred embodiment of the present invention, which further comprises a nasal inspiration and expiration part, wherein the central partition member is extended from the oral inspiration and expiration part to the nasal inspiration and expiration part.

Furthermore, in accordance with another preferred embodiment of the present invention, wherein the proximal inspiration channel and the distal expiration channel is connected to the nasal inspiration and expiration part respectively.

Furthermore, in accordance with another preferred embodiment of the present invention, which further comprises an inspiration tube and an expiration tube, wherein the inspiration tube is connected with the proximal inspiration channel and the nasal inspiration and expiration part, and the expiration tube is connected with the distal expiration channel and the nasal inspiration and expiration part.

As mentioned above, the present invention provides a medical bite block for user extending forward his lower jaw beyond his upper jaw in order to form the malposition of mouth shape even in a lying down position (supine position) after anesthesia, so that he could avoid the tongue fall down caused upper airway obstruction. Thus the risks that patients were brought to endoscopic inspection during anesthesia could be decreased.

The foregoing has outlined rather broadly the features and technical advantages of the present disclosure in order that the detailed description of the disclosure that follows may be better understood. Additional features and advantages of the disclosure will be described hereinafter, which form the subject of the claims of the disclosure. It should be appreciated by those skilled in the art that the conception and specific embodiment disclosed may be readily utilized as a basis for modifying or designing other structures or processes for carrying out the same purposes of the present disclosure. It should also be realized by those skilled in the art that such equivalent constructions do not depart from the spirit and scope of the disclosure as set forth in the appended claims.

BRIEF DESCRIPTION OF THE DRAWINGS

The novel features believed characteristic of the invention are set forth in the appended claims. The invention itself, however, as well as a preferred mode of use, further objectives and advantages thereof, will best be understood by reference to the following detailed description of an advantageous embodiment of the present invention when read in conjunction with the accompanying drawings, wherein:

DETAILED DESCRIPTION OF THE INVENTION

The detailed description provided below in connection with the appended drawings is intended as a description of the present examples and is not intended to represent the only forms in which the present example may be utilized or constructed. The description sets forth the functions of the example and the sequence of steps for constructing and operating the example. However, the same or equivalent functions and sequences may be accomplished by different examples.

Although the terms first, second, third, etc. may be used herein to describe various distance, longitudinal surface, and/or malposition, these distance, longitudinal surface, and/or malposition should not be limited by these terms. These terms may be only used to distinguish one distance, longitudinal surface or malposition from another distance, longitudinal surface or malposition. Terms such as "first," "second," and other numerical terms when used herein do not imply a sequence or order unless clearly indicated by the context. Thus, a first distance, longitudinal surface or malposition discussed below could be termed a second distance, longitudinal surface or malposition without departing from the teachings of the example embodiments.

Figure 1:
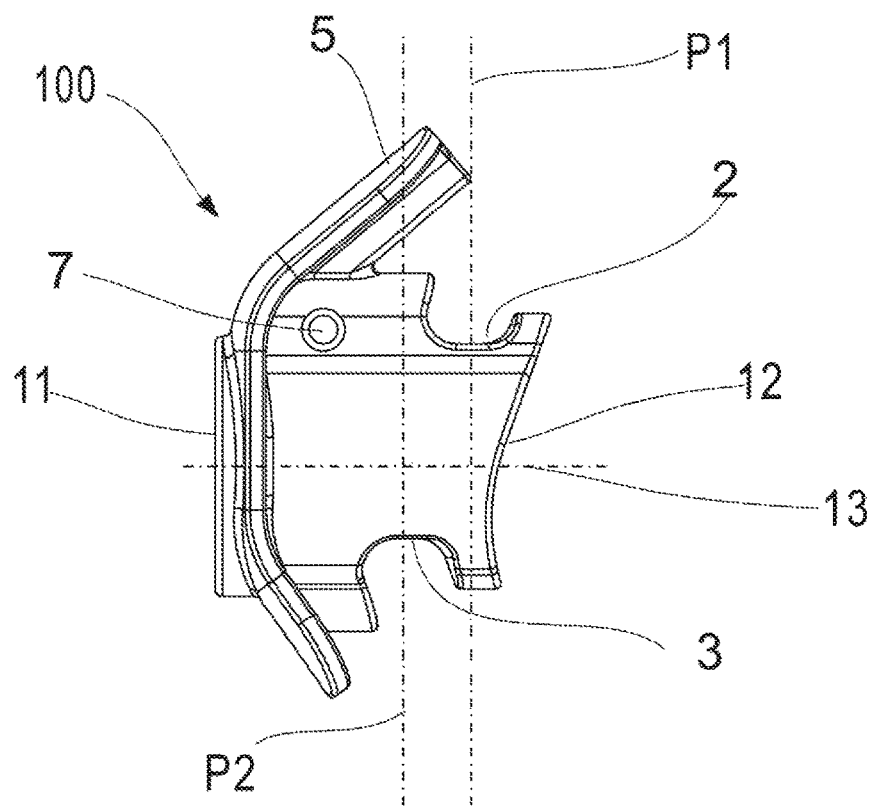
FIG. 1 illustrates the lateral view of an embodiment of the present invention.
Figure 2:
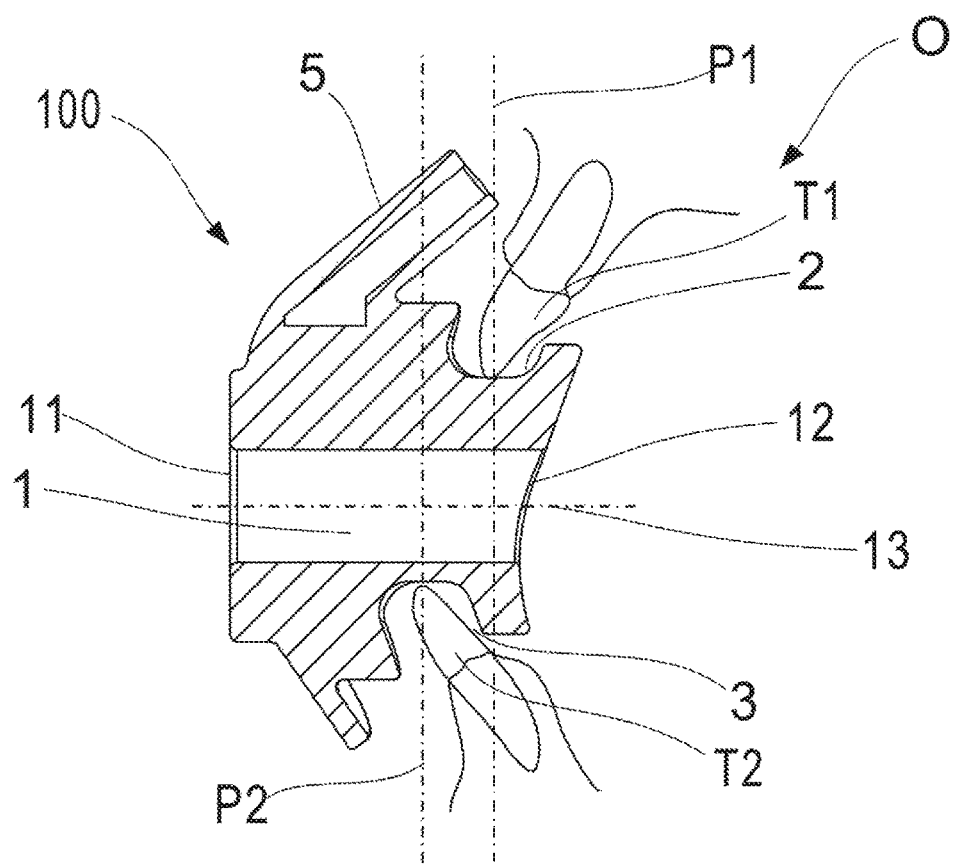
FIG. 2 illustrates the sectional view of an embodiment of the present invention with a schematic figure of a user's upper teeth and lower teeth being bitten.

With reference now to the figures, and in particular, with reference to FIG. 1, a diagram of a medical bite block is depicted in which an advantageous embodiment the present invention may be implemented. Additionally, FIG. 2 is a sectional view of a user's upper teeth and lower teeth being bitten in accordance with one embodiment of the present invention. The medical bite block 100 integrated as one-piece that is provided for a user to bite is inserted into and installed into the user's oral cavity O. The medical bite block 100 includes a through passageway 1, an upper biting groove 2, and a lower biting groove 3 at least. The through passageway 1 is penetrating through the medical bite block 100. One end of the through passageway 1 comprises an inlet opening 11, the other end comprises an oral opening 12. In addition, the oral opening 12 is used to connected with an oral cavity O of the user, and the inlet opening 11 is used to penetrate the endoscope device (figure is not shown). An upper surface of the medical bite block 100 provides the upper biting groove 2, and the upper biting groove 2 is provided for the upper teeth (maxillary teeth) T1, especially upper front teeth, to bite, engage and lock correspondingly. On the other hand, a lower surface of the medical bite block 100 provides a lower biting groove 3, and the lower biting groove 3 is provided for the lower teeth (mandibular teeth) T2, especially lower front teeth, to bite, engage and lock correspondingly. Additionally, the medical bite block would define a first distance from the upper biting groove 2 to the oral opening 12 along with the axis 13 and would define a second distance from the lower biting groove 3 to the oral opening 12 along with the axis 13. Thus, the second distance between the lower biting groove 3 and the oral opening 12 is greater than the first distance between the upper biting groove 2 and the oral opening 12, thereby the lower biting groove 3 is away from the oral cavity O of the user relative to the upper biting groove 2. Furthermore, the lower biting groove 3 and the upper biting groove 2 form a first malposition with each other corresponding to lower teeth T2 and upper teeth T1 respectively.

Figure 3:
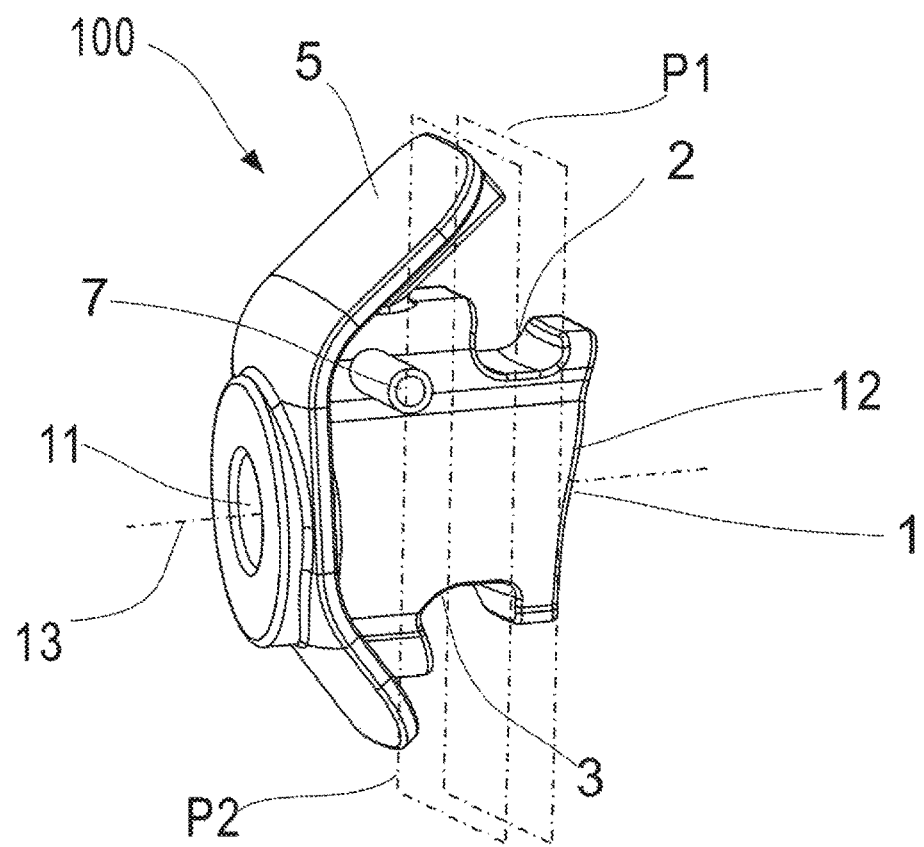
FIG. 3 illustrates the three-dimensional view of an embodiment of the present invention.
Figure 4:
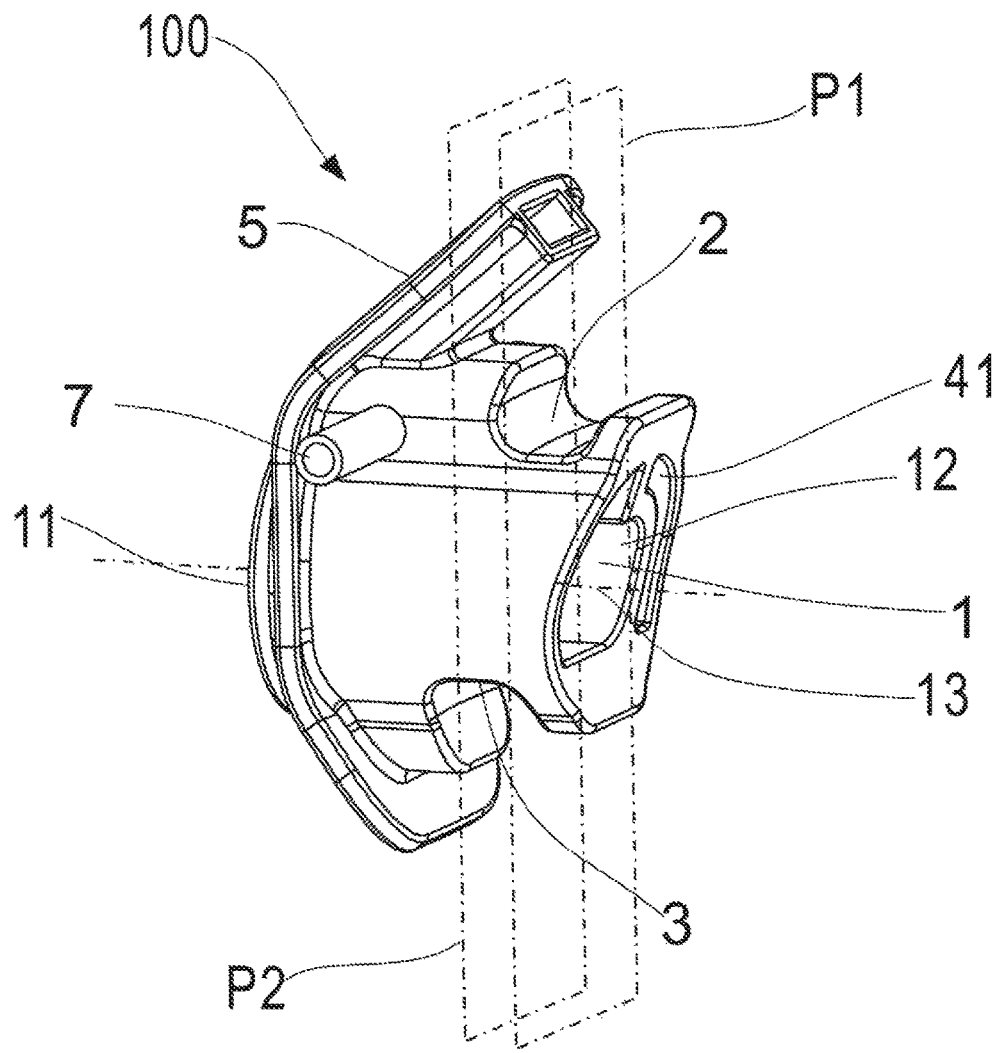
FIG. 4 illustrates another three-dimensional view of an embodiment of the present invention.

Moreover, please refer FIG. 2, FIG. 3 and FIG. 4, the upper biting groove 2 is perpendicular to an axis 13 of the through passageway 1, which further comprises a first longitudinal surface P1. Also, the lower biting groove 3 is perpendicular to an axis 13 of the through passageway 1, which further comprises a second longitudinal surface P2. Additionally, the first longitudinal surface P1 and the second longitudinal surface P2 is not overlapped but is corresponded, and the second distance between the second longitudinal surface P2 and the oral opening 12 is greater than the first distance between the first longitudinal surface P1 and the oral opening 12. A third distance between the first longitudinal surface P1 and the second longitudinal surface P2 is, for example but not limited to, 1 to 12 mm. That is to say, the third distance along with the axis 13 of the through passageway 1 between the upper biting groove 2 and the lower biting groove 3 is about 1 to 12 mm, but is not limited thereto.

As depicted therein, while the medical bite block 100 was installed into the mouth of the user, the upper biting groove 2 of the medical bite block 100 could be provided for receiving the user's upper teeth T1 bitten, engaged and locked. The lower biting groove 3 of the medical bite block 100 could be provided for the user's lower teeth T2 to bite, engage and lock. So that the user's upper teeth T1 and lower teeth T2 could bite, engage and lock the medical bite block 100 without requiring strenuous effort to extend forward the user's lower jaw beyond his upper jaw and his upper teeth. Furthermore, the user could use the medical bite block 100 to extend forward his lower jaw beyond his upper jaw and his upper teeth even in a lying down position (supine position) after anesthesia, especially after deep anesthesia, to avoid the tongue fall down caused upper airway obstruction. Therefore, the medical bite block of the present invention can decrease the risk of hypoxia during endoscopic inspection.

In addition, with reference now to FIG. 3, FIG. 4, FIG. 5 and FIG. 6, the present invention also comprises an inspiration tube 6 and an expiration tube 7 which are situated in the outer surface of the vertical direction of the inlet opening 11 and oral opening 12 respectively. Consequently, the user could have steady oxygen resource through inspiration tube 6 by oxygen providing system such as an oxygen cylinder or a liquid oxygen reservoir, and exhale the carbon dioxide from the nasal cavity and oral cavity through expiration tube 7 by the medical bite block 100 of the present invention. However, the present disclosure may not be limited thereto.

Figure 5:
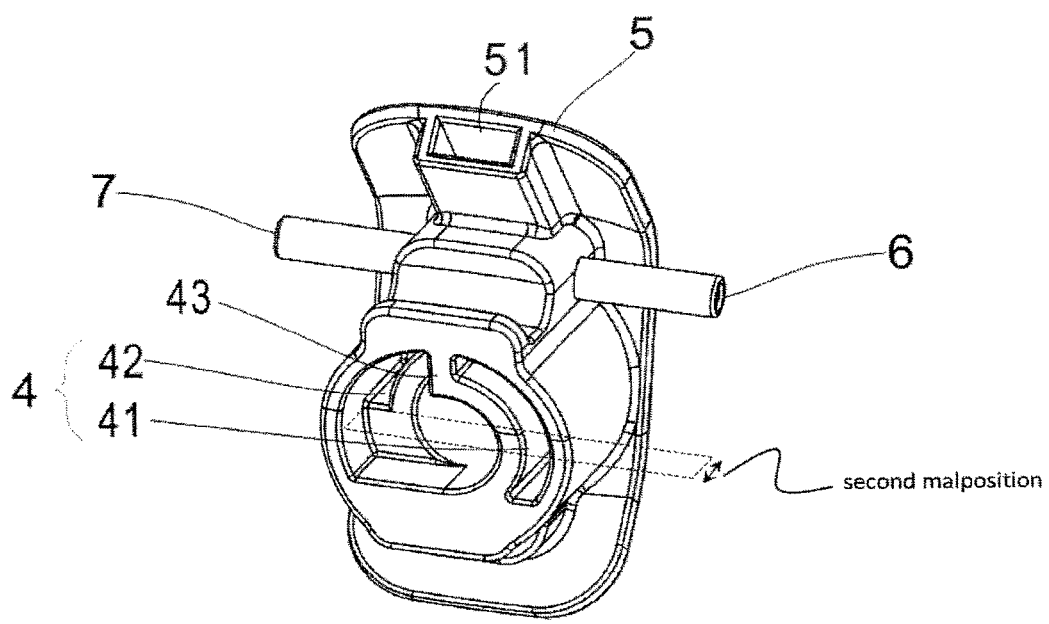
FIG. 5 illustrates the back view of an embodiment of the present invention.
Figure 6:
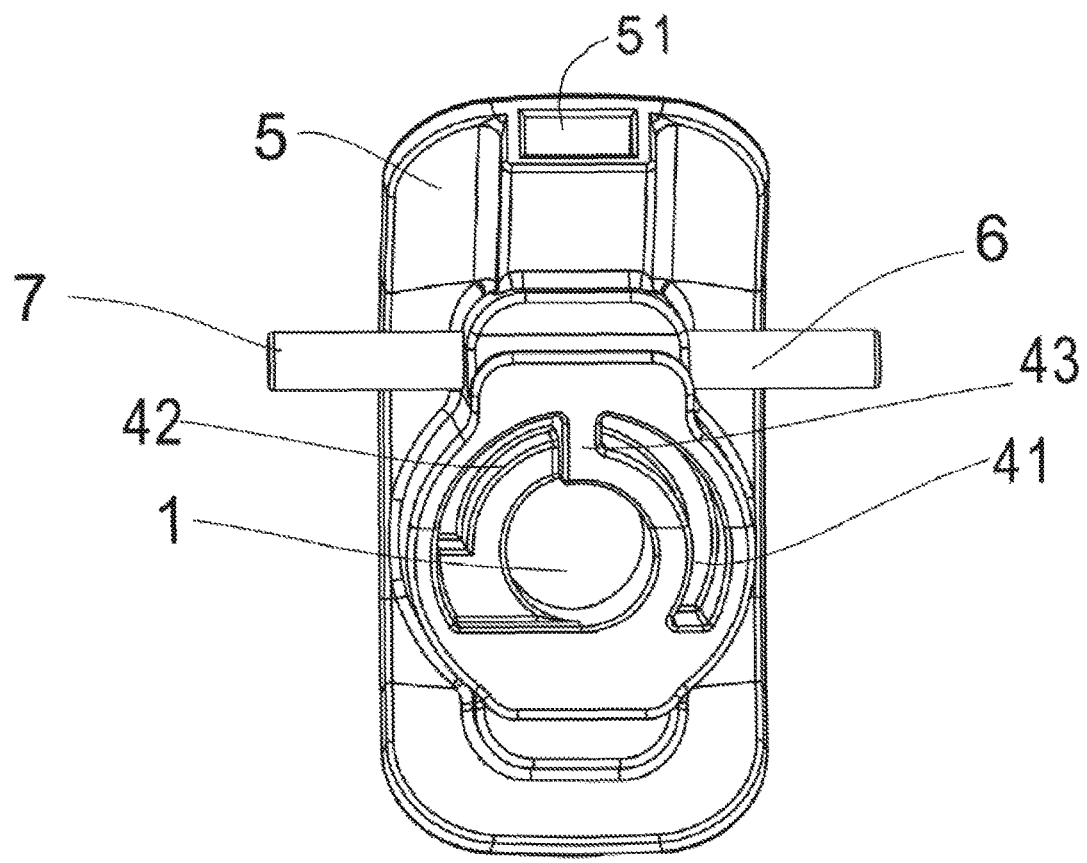
FIG. 6 illustrates another back view of an embodiment of the present invention.

In other embodiment, for example those shown in FIG. 4, FIG. 5 and FIG. 6, an oral inspiration and expiration part 4 is situated inside the inner wall of the through passageway 1 as a ring shape. The oral inspiration and expiration part 4 further comprises a proximal inspiration channel 41 and a distal expiration channel 42. In addition, the proximal inspiration channel 41 and the distal expiration channel 42, which form as the ring shape situated at the oral inspiration and expiration part 4 and are located adjacent to each other, further form a second malposition with one another. Next, the medical bite block would define a fourth distance from proximal inspiration channel 41 to the oral opening 12 along with the axis 13 and would define a fifth distance from the distal expiration channel 42 to the oral opening 12 along with the axis 13. Moreover, the fourth distance between proximal inspiration channel 41 and the oral opening 12 is shorter than the fifth distance between the distal expiration channel 42 and the oral opening 12, thus the distal expiration channel 42 is away from the oral cavity of the user relative to the proximal inspiration channel 41. Consequently, the proximal inspiration channel 41 and the distal expiration channel 42 form the second malposition with each other. In other instances, the proximal inspiration channel 41 and the distal expiration channel 42 further comprise a central partition member 43. The central partition member 43 is used to separate the proximal inspiration channel 41 from the distal expiration channel 42.

In another word, oxygen could be facilitated to be transported from inspiration tube 6 across the proximal inspiration channel 41 passing over oral cavity O to the upper respiratory tract of the user with a shorter distance than existed technique and product. So much so that the user could easily receive oxygen by the medical bite block of the present invention during anesthesia. Besides, the oxygen distributed in the proximal inspiration channel 41 and the carbon dioxide dispersed in the distal expiration channel 42 wouldn't mixed together due to the central partition member 43, so that the oxygen and the carbon dioxide could easily be inhaled and exhaled respectively by the proximal inspiration channel 41 and the distal expiration channel 42 while the user used the medical bite block 100 during endoscopic inspection after anesthesia.

In other hand, the present invention further comprises a nasal inspiration and expiration part 5 as shown in FIG. 4. The nasal inspiration and expiration part 5 is wing-shaped and is corresponded with the upper lip, that is the nasal inspiration and expiration part 5 is configured to establish a correspondence from the external nares to the upper lip vermillion. Furthermore, as seen in to FIG. 5 and FIG. 6, the nasal inspiration and expiration part 5 further comprises an inspiration and expiration duct 51. As a result, the user could inhale oxygen and exhale carbon dioxide more effectively by nasal inspiration and expiration part 5 of the present invention.

Certainly, the central partition member 43 is, but not limited to, extended from the oral inspiration and expiration part 4 to the nasal inspiration and expiration part 5. Hence, inspiration tube 6 is connected with the proximal inspiration channel 41 and nasal inspiration and expiration part 5. More accurately, the inspiration tube 6, the proximal inspiration channel 41, and the inspiration and expiration duct 51 are all specifically connected one another. As a consequence, the present invention could provide oxygen for user with shorter distance by proximal inspiration channel 41 and nasal inspiration and expiration part 5. On the other hand, the expiration tube 7 is connected with the distal expiration channel 42 and the nasal inspiration and expiration part 5. Namely, the expiration tube 7, the inspiration and expiration duct 51, and the distal expiration channel 42 are all specifically connected one another. To sum up, the present invention could provide oxygen to the oral cavity and nasal cavity of the user with shorter distance by proximal inspiration channel 41 and nasal inspiration and expiration part 5. Thus, the central partition member 43 is provided between the oral inspiration and expiration part 4 and the nasal inspiration and expiration part 5. In conclusion, the oxygen from the inspiration tube 6 could directly pass through proximal inspiration channel 41 and nasal inspiration and expiration part 5 in order to be supplied the user inhaling. On the contrary, the carbon dioxide would be removed from distal expiration channel 42 and nasal inspiration and expiration part 5 through expiration tube 7 to be expelled from the medical bite block 100.

As set out above, the user could use his upper teeth T1 and lower teeth T2, especially his upper front teeth and lower front teeth, to bite, engage and lock the upper biting groove 2 and the lower biting groove 3 respectively. In another word, it is characterized by the user's lower jaw extending out, causing his lower front teeth to sit in front of his upper front teeth, while the user could use the medical bite block 100 of the above-mentioned present invention even in a lying down position (supine position) after anesthesia, especially after deep anesthesia, to avoid the tongue fall down caused upper airway obstruction and further can reduce the chances of hypoxia. Besides, the inspiration tube 6, the proximal inspiration channel 41 and the nasal inspiration and expiration part 5 are all specifically connected one another, so that the present invention could more effectively provide oxygen for user with a shorter distance in particular.

In the description above, numerous specific details are set forth. However, it is understood that embodiments of the invention may be practiced without these specific details. For example, well-known equivalent components and elements may be substituted in place of those described herein, and similarly, well-known equivalent techniques may be substituted in place of the particular techniques disclosed. In other instances, well-known structures and techniques have not been shown in detail to avoid obscuring the understanding of this description.

Reference in the specification to "an embodiment," "one embodiment," "some embodiments," or "other embodiments" means that a particular feature, structure, or characteristic described in connection with the embodiments is included in at least some embodiments, but not necessarily all embodiments. The various appearances of "an embodiment," "one embodiment," or "some embodiments" are not necessarily all referring to the same embodiments. If the specification states a component, feature, structure, or characteristic "may", "might", or "could" be included, that particular component, feature, structure, or characteristic is not required to be included. If the specification or claim refers to "a" or "an" element, that does not mean there is only one of the element. If the specification or claims refer to "an additional" element, that does not preclude there being more than one of the additional element.

Although the present invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the scope of the present invention.

What is claimed is:

1. A medical bite block, which is integrated as one-piece and is provided for a user to bite and is inserted into the user's mouth, wherein the medical bite block includes:
    a through passageway, which is penetrating through the medical bite block, wherein one end of the through passageway comprises an inlet opening, the other end comprises an oral opening, wherein the oral opening is configured to connect with an oral cavity of the user;
    an upper biting groove, wherein an upper surface of the medical bite block provides the upper biting groove; and
    a lower biting groove, wherein a lower surface of the bite block provides the lower biting groove,
    wherein a second distance between the lower biting groove and the oral opening is greater than a first distance between the upper biting groove and the oral opening, thereby the lower biting groove is away from the oral cavity of the user relative to the upper biting groove and provides a first malposition between the lower biting groove and the upper biting groove,
    wherein the medical bite block comprises an oral inspiration and expiration part, wherein the oral inspiration and expiration part is located inside an innerwall of the through passageway as a ring shape, and
    wherein the oral inspiration and expiration part further comprises an inspiration channel and an expiration channel, wherein the inspiration channel and the expiration channel form a second malposition with each other, wherein the inspiration channel and the expiration channel are located adjacent to each other and formed as the ring shape of the oral inspiration and expiration part.

2. The medical bite block of claim 1, wherein the upper biting groove is perpendicular to an axis of the through passageway, which further comprises a first longitudinal plane; wherein the lower biting groove is perpendicular to the axis of the through passageway, which further comprises a second longitudinal plane; wherein the first longitudinal plane and the second longitudinal plane do not overlap.

3. The medical bite block of claim 1, wherein a third distance between the first longitudinal plane and the second longitudinal plane is 1 to 12 mm.

4. The medical bite block of claim 1, wherein the expiration channel is away from the oral cavity of the user relative to the inspiration channel and form the second malposition with each other.

5. The medical bite block of claim 1, which further comprises a central partition member, wherein the central partition member is used to separate the inspiration channel from the expiration channel.

6. The medical bite block of claim 1, which further comprises an inspiration tube and an expiration tube, wherein the inspiration tube is connected with the inspiration channel, wherein the expiration tube is connected with the expiration channel.

* * * * *